United States Patent [19]

Akiyama et al.

[11] Patent Number: 5,162,057
[45] Date of Patent: Nov. 10, 1992

[54] COATINGS FOR STABLE SUSTAINED RELEASE PREPARATIONS

[75] Inventors: Yohko Akiyama, Ibaraki; Naoki Nagahara, Sakai; Minoru Yoshioka, Mukoo, all of Japan

[73] Assignee: Takeda Chemical Industries, Ltd., Osaka, Japan

[21] Appl. No.: 659,610

[22] Filed: Feb. 22, 1991

[30] Foreign Application Priority Data

Feb. 23, 1990 [JP] Japan .................................. 2-42825

[51] Int. Cl.⁵ ...................... C09D 171/00; A61K 9/24; A61K 9/42; A61K 47/00
[52] U.S. Cl. .................................. 106/243; 106/211; 106/244; 106/245; 106/268; 106/270; 424/472; 424/476; 514/770; 514/777; 514/778; 514/784; 514/786
[58] Field of Search ................ 106/211, 215, 243–245, 106/270, 268; 514/770, 772, 777, 778, 784, 786; 424/476, 472

[56] References Cited

U.S. PATENT DOCUMENTS 3,097,144  7/1963  Banker ................................. 106/268
3,244,596  4/1966  Lach ..................................... 106/243
3,914,131 10/1975  Hutchison ........................... 106/268

FOREIGN PATENT DOCUMENTS 261192    4/1964  Australia ............................ 424/476
61-12632  1/1986  Japan .................................. 514/786

OTHER PUBLICATIONS

"Polyglycerol Esters," Sakamoto Chemicals Ind., Ltd., May 2, 1986, p. 12.

Primary Examiner—Theodore Morris
Assistant Examiner—David M. Brunsman
Attorney, Agent, or Firm—Wegner, Cantor, Mueller & Player

[57] ABSTRACT

Fatty acid esters of polyglycerols, such as stearic acid penta(tetra)glyceryl ester, behenic acid hexa(tetra)glyceryl ester, lauric acid mono(deca)glyceryl ester, oleic acid di(tri)glyceryl ester, linolic acid di(hepta)glyceryl ester, palmitic acid deca(deca)glyceryl ester, etc. are employed as coating agents for coating solid preparations such as tablets, pills, granules, fine granules, etc. By coating with the coating agents, stable sustained release of active ingredients contained in the preparations is obtained, even after a long period of storage.

31 Claims, No Drawings

COATINGS FOR STABLE SUSTAINED RELEASE PREPARATIONS

This invention relates to coating agents, which are usable in coating solid preparations, such as fine granules, granules, pills and tablets, and also to preparations which are coated with the same.

From the standpoint of effectively utilizing the active ingredients, it is considered important to process such non-active ingredients into sustained release preparations, that provided the specific rate of release being suited for individual active ingredients to thereby sustain their efficacies or suppress abrupt rise of their blood concentrations, resulting in reduction of the number administrations or alleviation of their side effects; to mask bitter or unpleasant tasted active ingredients; or to reform the surface of the active ingredients to thus impart a varied degree of surface wetting.

In order to control the release of drug substances from solid preparations, to modify the surfaces of drug substances or to mask the taste of drug substances, it has already been conducted into practice to coat solid preparations, such as fine granules, granules, pills and tablets with waxes. However, there are only a few reports about the methods for maintaining release-sustaining ability of drugs, and it has not been known at all to use fatty acid esters of polyglycerol for the method.

Provision of coating with use of conventional waxes always involves time-course deterioration in quality and properties of the resulting coating films. And, since it also involves generation of static electricity during the coating operation, formation of unstable films and difficulty in film coating results. Such wax coatings, particularly when provided for the purpose of release control, causes great adverse effects, such as varied rates of release of drug substance, on the resultant coating films. Heretofore, great difficulties have been encountered both in developing a method of preventing or suppressing the time-course deterioration of the resultant coating films In light of the above, the present inventors conducted search and investigation into a coating agent that can function as a coating film without undergoing time-course deterioration, and as a result, obtained coating agents which consist of or contain fatty acid esters of polyglycerol. These said coating agents, when applied to solid preparations such as pills, granules or fine granules, were unexpectedly found to produce coated preparations markedly stable in release-sustaining properties. In particular, when used in providing a coating for the purpose of release control, the coating agents were able to yield preparations extremely stable in sustained release properties yet being free from any time-course change in the release of drug substances from the coated preparations.

This invention has been completed on the basis of such findings, and is concerned with the coating agents consisting of or containing fatty acid esters of polyglycerol and also solid preparations coated with the coating agents.

The fatty acid esters of polyglycerol, which are usable in this invention, comprise esters of polyglycerols with fatty acids. The term "polyglycerol" designates "polyhydric alcohols which, in the molecule, have n (cyclic) to n+2 (straight-chain and branched) of hydroxyl groups and n−1 (straight-chain and branched) to n (cyclic) of ether linkages" (refer to "Polyglycerol Esters", edited and published (as of May 2, 1986) by Sakamoto Chemicals Ind., Ltd. of Japan, pp. 12), and as the said polyglycerol, for example, there are used compounds as represented by the formula:

$$HO-(CH_2-\underset{\underset{OH}{|}}{CH}-CH_2-O)_n-H \qquad [I]$$

wherein n is a degree of polymerization. The n is normally an integer of 2 to 40, preferably 2 to 10. Referring to specific examples of such polyglycerols, frequent use is made of, for example, diglycerol, triglycerol, tetraglycerol, pentaglycerol, hexaglcyerol, heptaglycerol, octaglycerol, nonaglycerol, decaglycerol, etc., with tetraglycerol and hexaglycerol being utilized frequently. As the fatty acid, for example, there can be used saturated or unsaturated higher fatty acids having a number of carbon atoms of 8 to 40, preferably 12 to 22. As the said fatty acids, there are utilized, for example, palmitic acid, stearic acid, oleic acid, linolic acid, linolenic acid, myristic acid, lauric acid, ricinolic acid, caprylic acid, capric acid and behenic acid. In particular, frequently utilized are stearic acid, oleic acid, lauric acid, behenic acid and ricinolic acid. With reference to the fatty acid esters of polyglycerol, use is made of monoesters or polyesters of the polyglycerols with the fatty acids as described above, and such fatty acid esters of polyglcyerol normally have a molecular weight of 200 to 5,000, preferably 300 to 2,000, more preferably 500 to 2,000, while they ordinarily show an HLB (hydrophilic-lipophylic balance) value of 1 to 22, preferably 1 to 15, more preferably 2 to 9. Also, the fatty acid esters of polyglycerol can suitably be selected, based upon the kind of active ingredients to be used as well as the type of preparations subjected to coating. Generally employed are a solid form at a room temperature (about 15° C.), having a melting point of 15 to 70° C., preferably 45 to 70° C. The fatty acid ester of polyglyceride employed in present invention may be a mixture of at least two kinds of the ester, and in this case, at least one kind of liquid fatty acid ester of polyglyceride may be used as far as the mixture is a solid form at the room temperature. As specific examples of the fatty acid esters of polyglycerol, there are used, either alone or as a mixture of more than two kinds of esters, such as stearic acid mono(di)glyceryl ester, behenic acid hexa(tetra)glyceryl ester, caprylic acid di(tri)glyceryl ester, capric acid di(tri)glyceryl ester, caprylic acid mono(deca)glyceryl ester, lauric acid mono(deca)glyceryl ester, lauric acid mono(tetra)glyceryl ester, oleic acid di(tri)glyceryl ester, oleic acid di(tetra)glyceryl ester, linolic acid di(tri)glyceryl ester, linolic acid di(tetra)glyceryl ester, linolic acid di(hexa)glyceryl ester, linolic acid di(hepta)glyceryl ester, stearic acid mono(deca)glyceryl ester, stearic acid deca(deca)glyceryl ester, stearic acid mono(tetra)glyceryl ester, stearic acid mono(hexa)glyceryl ester, stearic acid sesqui(hexa)glyceryl ester, stearic acid tri(hexa)glcyeryl ester, stearic acid penta(hexa)glyceryl ester, oleic acid sesqui(deca)glyceryl ester, oleic acid penta(hexa)glyceryl ester, oleic acid mono(hexa)glyceryl ester, oleic acid mono(deca)glyceryl ester, oleic acid deca(deca)glyceryl ester, lauric acid mono(deca)glyceryl ester, stearic acid tri(mono)glyceryl ester, stearic acid penta(tetra)glyceryl ester, oleic acid mono(tetra)glyceryl ester, oleic acid penta(tetra)glyceryl ester, lauric acid mono(tetra)glyceryl ester, palmitic acid mono(deca)glyceryl ester, palmitic acid deca(deca)glyceryl ester, palmitic acid mono(hexa)glyceryl ester, palmitic acid sesqui(hexa)glyceryl ester, palmitic acid tri(hexa)glyceryl ester, palmitic acid penta(hexa)glyceryl ester, palmitic acid mono(tetra)glyceryl ester, palmitic acid tri(tetra)glyceryl ester and palmitic acid penta(tetra)glyceryl ester. Among these esters, frequently used is, for example, stearic acid penta(tetra)glyceryl ester (e.g., PS-310 produced by Sakamoto Chemicals Ind., Ltd. of Japan, etc.), stearic acid mono(tetra)glyceryl ester (e.g., MS-310 produced by Sakamoto Chemicals Ind., Ltd. of Japan, etc.), stearic acid penta(hexa)glyceryl ester (e.g., PS-500 produced by Sakamoto chemicals Ind., of Japan, etc.), stearic acid sesqui(hexa)glyceral ester (e.g., SS-500 produced by Sakamoto Chemicals Ind., Ltd. of Japan, etc.) stearic acid mono(deca)glyceryl ester, or a mixture thereof.

The coating agents according to this invention can be prepared according to conventional methods, and may be prepared using fatty acid esters of polyglcyerol solely, but may also be prepared using, together with the same, other components as conventionally used for coatings. The present invention further includes preparations coated with these coating agents as well as coating films (films formed by the coating) themselves obtained by coating preparations with these coating agents. The coating films preferably melt in the range of from 40 to 120° C.

The above-described other components may be exemplified by polymeric materials, and as these polymeric materials, there may be mentioned, for example, hydroxypropyl cellulose (as specified in the Japanese Pharmacopeia, 11th revised edition, which is hereinafter referred to briefly as "JP 11"), hydroxypropyl methylcellulose (TC-5E, TC-55R, produced by Shin-etsu Chemical Ind., Co. of Japan), polyvinyl acetal diethylaminoacetate (AEA, produced by Sankyo Co. of Japan, as specified in the Standards 1986 out of the Scope of the Japanese Pharmacopeia), aminoalkyl methacrylate copolymer (Eudragit E 100, produced by Roehm Pharma of West Germany, which is hereinafter referred to briefly as "RP"), hydroxypropyl methylcellulose phthalate (as specified in JP 11), hydroxypropyl methylcellulose acetate succinate (produced by Shin-etsu Chemical Ind., Co. of Japan), carboxymethyl ethylcellulose (CMEC, produced by Freund Sangyo Co. of Japan, as specified in the Standards 1986 out of the Scope of the Japanese Pharmacopeia), methacrylate copolymer L (Eudragit L 100 produced by RP), methacrylate copolymer L-D (Eudragit L-30-D-55, produced by RP), methacrylate copolymer S (Eudragit S 100, produced by RP), aminoalkyl methacrylate copolymer (Eudragit RS, RN 100L, RSPML, RN 100, RSPM, produced by RP), cellulose acetate trimellitate (produced by Eastman Chemicals), polyvinyl acetate phthalate (COLORCON), cellulose acetate phthalate (as specified in JP 11), ethylcellulose (FMC-Asahi Chemical Ind. of Japan) and Eudragit NE 30-D (produced by RP), Carbopole (produced by Goodrich Co., U.S.A.), etc. These can be mixed with the fatty acid ester of polyglycerol, either alone or as a mixture with at least two of these other components.

The polymeric materials may normally be added to the fatty acid polyglycerol ester at a ratio of 0.0001 to 100 g per g of the latter, preferably 0.01 to 10 g, more preferably 0.01 to 2.5 g.

Furthermore, the coating agent according to this invention may contain a lipid or wax having a softening point or melting point of 40 to 120° C., desirably 40 to 90° C. Examples of such lipids or waxes include beeswax, carnauba wax, spermaceti, lecithin, paraffin and microcrystalline wax, or fatty acids, such as stearic acid and palmitic acid, or their salts (e.g., salts with sodium, potassium, etc.), and higher fatty alcohols, such as stearyl alcohol, cetyl alcohol and the like.

The lipids or waxes, alone or as a mixture with at least two lipids or waxes, may be mixed with the fatty acid esters of polyglycerol. The desired mixing ratio is 0.0001 to 100 g per g of the fatty acid polyglyceryl ester, preferably 0.01 to 10 g, more preferably 0.01 to 2.5 g.

Consequently, the content of the fatty acid ester of polyglycerol in the coating agent according to this invention normally is 14 to 100 % (w/w), preferably 20 to 100%, more preferably 20 to 60%.

When the coating agent according to this invention is provided to such solid preparations as fine granules, granules, pills and tablets, the release of active ingredients contained in the solid preparations is controlled, the sustained release of the ingredient is sustained for a long period of time (about 0.5 to 48 hours) changes in the sustained release property over time is prevented, and also the taste the preparation is masked.

The active ingredient can suitably be selected. Examples of the active ingredients, which are ordinarily used as a drug for humans, include phenylpropanolamine hydrochloride, chlorpheniramine maleate, phenylephrine hydrochloride, theophylline, caffeine, procainamide hydrochloride, cefalexin, ampicillin, molsidomine, indomethacin, sulfisoxazole, sulfadiazine, diazepam, valproic acid, quinidine, aspirin, 3,4-dihydro-2,8-diisopropyl-3-oxo-2H-1,4-benzoxazine-4-acetic acid (hereinafter referred to briefly as "AD-5467"), derapril hydrochloride, ipuriflavone, trepibutone, de(N-methyl)-N-ethyl-8,9-anhydroerythromycin A 6,9-hemiacetal, isosobide nitrate, ketoprofen, cyclanderate, idebenone, 2-(12-hydroxydeca-5,10-diynyl)-3,5,6-trimethyl-1,4-benzoquinone (hereinafter referred to briefly as "AA-861"), salicylic acid, ibuprofen, epinephrine, haloperidol, reserpine, ascorbic acid, acetaminophen, probenicide, vinpocetine, estazolam, acetazolamide, paraverine, tolbutamide, propranolol, morphine, ephedrine, scopolamine, chloropromazine, manidipin hydrochloride, serratiopeptidase, r-FGF, IL-2, insulin, interferon and SOD. These active ingredients are contained in solid dosage forms at a ratio of 0.0001% to 95% (w/w), preferably 0.1% to 90% (w/w).

Among the solid dosage forms which are usable in this invention, fine granules can be manufactured by use of a known granulator, etc. and normally show a grain size distribution of not less than 75 weight % for particles of 500 to 10 um, less than 5 weight % for particles of not less than 500 um and less than 10 weight % for particles of not more than 10 um, preferably not less than 75 weight % for particles of 500 to 105 $\mu$m, less than 5 weight % for particles of not less than 500 $\mu$m and less than 10 weight % for particles of less than 74 $\mu$m. Also, granules can be produced by means of the known procedures and show, for example, a grain size distribution of not less than 90 weight % for particles of 1410 to 500 $\mu$m and less than 5 weight % for particles of less than 177 um. Pills and tablets can also be manufactured by means of the known procedures, whereupon pills weigh 0.1 g per pill and tablets have a diameter of 2 mm to 30 mm, preferably 5 mm to 20 mm.

As the effective ingredients which may be contained in these solid dosage forms, there are used drug substances for veterinary use and feedstuff additives in addition to the drugs designed for use toward humans. These include for example, macrolide antibiotics, such as tilosin and sedecamycin; tetracycline antibiotics, such as chlortetracycline; penicilin antibiotics; cephalosporin antibiotics; aminoglycoside antibiotics, such as hygromycin; polypeptide antibiotics, such as enramycin; polyether based antibiotics, such as chloramphenicol and florfenicol; synthetic antimicrobial and antiprotozoan agents, such as monesin and benofloxacin; enzymes, such as serratiopeptidase, phycomyces lipase, trypsin, diastase and cellulase; dried live bacterial powders, such as Lactobacillus acidophilus and Lactobacillus bifidus; minerals, such as potassium iodide, calcium iodate, ferrous sulfate and ferrous maleate; and vitamins (e.g., thiamine, pyridoxine, menadione, folic acid and nicotinic acid), either alone or as a mixture of at least two ingredients. The content of these effective ingredients in the solid dosage forms range from 0.00001% to 95% (w/w), preferably from 0.01% to 90% (w/w).

Solid agrochemical preparations, such as granules, when they contact with water after being scattered, in some instances undergo rapid elution of the formulated active ingredients in higher concentrations than required to produce its biological effects. In such case, phytocidal actions on crops, such as withered leaves and suppressed growth, take place, or eluted agrochemical active ingredients decompose or disappear rapidly in water or soil, sometimes resulting in failure to demonstrate the intended biological effects of the active ingredients. Therefore, the coating agent of this invention can also be applied in the field of agrochemicals so as to permit the active ingredients to be released at such a rate that they may produce the expected efficacies. As these agrochemical active ingredients, there can be utilized, either alone or as a mixture of more than two ingredients, such insecticides as pyridaphenthion, chlorpyrifos-methyl, rotenone, dicofol, benzomate, cartap and buprofezin; fungicides, such as varidamycin A, streptomycin, oxytetracycline, novobiocin, mildiomycin, copper sulfate, captran and polycarbamate; herbicides, such as phenothiol, simazine, prometryn, pyrazolate, paraquat, glyphosphate and alachlor; and plant growth regulating agents, such as ancymidor, indoleacetic acid, ethychlozate, oxyethylenated higher alcohols and chlormequat. The contents of agrochemical active ingredients in solid preparations range from 0.0001% to 95% (w/w), preferably from 0.01 % to 90% (w/w).

The coating agents according to this invention may also be applied in the field of food products by blending them with one kind or plural kinds of food additives, such as 5'-ribonucleotides, dried yeast extracts, citric acid and tartaric acid; amino acids, such as methionine and lysine hydrochloride; flavors, such as extracts of dried mushroom and dried bonito; vitamins, such as thiamine, pyridoxin, menadione, folic acid, ascorbic acid, nicotinic acid, tocopherols and vitamin A; minerals, such as potassium iodide, calcium iodate, ferrous sulfate and ferrous fumarate; and components contained in health food products or nutritionally functional food products, such as fructo-oligosaccharides, erythropoietin, glutathion, taurine, bifidus microbes, soybean lecithine and inositol to thereby process the mixtures into solid preparation forms containing 0.0001% to 95% (w/w), preferably 0.01 % to 90% (w/w).

In the coating-application of the coating agents of this invention, if necessary, other ingredients as generally used in the coating practice can be employed, such as surfactants and polymeric materials being exemplified by polyvinyl pyrrolidone, methylcellulose and carboxymethyl-cellulose as well as other solid additives being exemplified by talc, light anhydrous silicate, magnesium stearate, Kaolin, starch, crystalline cellulose, lactose, mannitol, sorbitol, fine granulated sugar, anhydrous calcium phosphate, etc. The above-mentioned ingredients or additives may be used in the coating application, either after being mixed (for example, in an amount of 30 to 50 weight %, in the case of the solid additives) with the present coating agent, or by separately applied to the solid preparations without such mixing.

In conducting the said coating-application, the per se known procedures can be employed. Namely, coating may be carried out by the pan coating method, fluidized-coating method or centrifugal fluidized-coating method. The coating may be carried out by a procedure of spraying, etc. in the case where the coating agent is prepared as a liquid wherein the agent and/or other ingredients are dispersed or dissolved in water (the ratio of water: 40 to 90 weight %) or organic solvents (e.g. alcohols, such as methanol, ethanol, isopropyl alcohol, etc.; ketones, such as acetone, etc.; hydrogenated hydrocarbons, such as, chloroform, dichloromethane, trichloroethane, etc.).

Alternatively, the present coating agent is prepared in the form of an emulsion by melting and mixing the agent with other additives such as a fatty acid ester of polyglycerol, or the like by heating, and then mixing with water to allow emulsification. The emulsion thus prepared can be sprayed on the surface of a solid preparation and dried to obtain a coated preparation. Further, the present coating agent can be applied for coating by charging the agent into solid preparations which are preheated through warm air in an apparatus such as a coating pan, followed by melting and spreading the coating agent.

The solid preparations desirably are coated normally at a temperature of 25° to 60° C., preferably 25° to 40° C.

The length of time required for the coating can suitably be selected, taking into consideration the method of coating, properties and quantity of the coating agent to be used, properties of the solid preparation, etc.

The required amount of the coating agent of this invention is in the proportions of 0.1 to 30 5 (w/w), preferably 0.5 to 10% (w/w), of the tablet weight in the case of tablets; 0.1% to 50% (w/w), preferably 1% to 20% (w/w), in the cases of pills and granules; and 0.1% to 100% (w/w), preferably 1% to 50% (w/w), in the case of fine granules.

The coated preparations according to this invention as obtained by above procedures possess the excellent effects, such as:

(1) To have the controlled rate of release of the active ingredients, which rate of release does not change for a long period of time;

(2) To mask the bitter or unpleasant taste of the active ingredients;

(3) To permit the number of administrations to decrease, for increasing patient convenience and compliance; and (4) To enable side effects of the active ingredients to be alleviated.

In other words, the coated preparations prepared by employing, present coating agent are entirely free from any change or deterioration in properties of the coating films during storage for a prolonged period of time; when the coating is provided for the purpose of sustaining the release, the resulting coated preparations are extremely stable, remaining unchanged in the rate of release of drug substances for a long period of time; and in cases where the coating is provided for the purposes of masking and surface modification, the resulting coated preparations can maintain the intended functions without undergoing any change for a long time.

In addition, the said coated preparations can be used and applied in the same manner as the conventional preparations (or solid preparations).

Present invention is further explained by the following Examples.

EXAMPLE 1

(1) a 100 g quantity of Nonpareil 101 (produced by Freund Sangyo KK of Japan) was sprayed with a mixture consisting of 100 g each of phenylpropanolamine hydrochloride and corn starch and distilled water alternately in an coating machine at a revolution speed of 400 rpm and at a temperature of blown air of 50° C., with the temperature of the material being maintained at 40° C., followed by drying under reduced pressure (ca. 5 mmHg) at 40° C. to produce 270 g of granules having a size of 670 μm to 1110 μm which were coated with phenylpropanolamine.

(2) A 270 g quantity of the granules as described above was sprayed with a solution of 50 g of stearic acid penta(tetra)glyceride ester in 300 ml of methylene chloride at a rate of 5 ml per minute, while the material was maintained at a temperature of 35° C., to thereby give 260 g of coated granules having a grain size of below 1190 μm which were coated with stearoyl penta(tetra)-glyceride at a ratio of 8% to the granule.

EXAMPLE 2

Granules (83 g) obtained in Example 1 (1) were sprayed with a solution of stearic acid mono(tetra)-glyceryl ester (66 g) in methylene chloride (200 ml) at a rate of 2 ml per minute maintaining the temperature of the granules at 35° C. to obtain coated granules (100 g) having a size of not more than 1000 μm and being coated with stearyl mono(tetra)glyceride in an amount of 19% (w/w) to the granules.

The granules thus obtained were subjected to dissolution test in an aqueous solution (900 ml) containing 0.007% of sodium dodecyl sulfate, according to "The Method for Determining Dissolution (paddle method)" provided in The Japanese Pharmacopeia, Revised Ed. 11.

The results of the dissolution tests with the initial granules and with those after storage of one week are shown in the following Table;

| Dissolution rate | 15 minutes | 30 minutes | 1 hour |
| --- | --- | --- | --- |
| Initial granules | 52.6% | 84.1% | 95.6% |
| after 1 week storage | 52.3% | 84.1% | 97.8% |

As seen from the Table, the granules were stable showing unchanged dissolution rates even after the storage.

EXAMPLE 3

Granules (83 g) obtained in Example 1 (1) were sprayed with a dispersion of stearic acid penta(tetra)-glyceryl ester (66 g) and talc (66 g) in methylene chloride at a rate of 2 ml per minute, maintaining the temperature of the granules at 35° C. to obtain coated granules (80 g) having a size of not more than 1000 μm and being coated with the solid ingredients in a ratio of 36% to the granules.

The coated granules thus obtained were subjected to dissolution test in the same manner as in Example 2. The results are shown in the following Table.

| | Dissolution rate | |
| --- | --- | --- |
| 3 hours | 6 hours | 10 hours |
| 11.3% | 42.4% | 67.3% |

We claim:

1. In a sustained release composition comprising a solid preparation coated with a coating agent, the improvement wherein said coating agent comprises a fatty acid ester of polyglycerol.

2. The sustained release composition according to claim 11, wherein the coating agent further comprises a lipid or a wax.

3. The sustained release composition according to claim 2, wherein said lipid or wax is selected from the group consisting of paraffin, microcystalline wax, a higher fatty acid and a higher alcohol.

4. The sustained release composition according to claim 2, wherein said lipid or wax is selected from the group consisting of stearic acid and palmitic acid.

5. The sustained release composition according to claim 2, wherein said lipid or wax is stearyl alcohol.

6. The sustained release composition according to claim 2, wherein said lipid or wax is selected from the group consisting of paraffin and microcrystalline wax.

7. The sustained release composition according to claim 11, wherein the coating agent has a melting point of from 40° to 120° C.

8. The sustained release composition according to claim 1, wherein the fatty acid ester of polyglycerol is solid at room temperature.

9. The sustained release composition according to claim 1, wherein the melting point of the fatty acid ester of polyglycerol is in the range of 15° to 70° C.

10. The sustained release composition according to claim 1, wherein the melting point of the fatty acid ester of polyglycerol ranges from 45° to 70° C.

11. The sustained release composition according to claim 1, wherein the fatty acid ester of polyglycerol has an HLB value from 1 to 15.

12. The sustained release composition according to claim 1, wherein the fatty acid ester of polyglycerol has an HLB value from 2 to 9.

13. The sustained release composition according to claim 1, wherein a degree of polymerization of the polyglycerol of said fatty acid ester of polyglycerol ranges from 2 to 40.

14. The sustained release composition according to claim 1, wherein a degree of polymerization of the polyglycerol of said fatty acid ester of polyglycerol ranges from 2 to 10.

15. The sustained release composition according to claim 1, wherein the polyglycerol of said fatty acid ester of polyglycerol is selected from the group consisting of diglycerol, tetraglycerol, hexaglycerol, heptaglycerol and decaglycerol.

16. The sustained release composition according to claim 1, wherein the polyglycerol of said fatty acid ester of polyglycerol is selected from the group consisting of diglycerol, tetraglycerol and hexaglycerol.

17. The sustained release composition according to claim 11, wherein the polyglycerol of said fatty acid ester of polyglycerol is tetraglycerol.

18. The sustained release composition according to claim 11, wherein the fatty acid of said fatty acid ester of polyglycerol is selected from the group consisting of caprylic acid, lauric acid, myristic acid, palmitic acid, stearic acid, oleic acid, linolic acid, ricinolic acid, ricinoleic acid and behenic acid.

19. The sustained release composition according to claim 1, wherein the fatty acid of said fatty acid ester of polyglycerol is a saturated fatty acid.

20. The sustained release composition according to claim 19, wherein the saturated fatty acid is selected from the group consisting of caprylic acid, lauric acid, stearic acid, palmitic acid and behenic acid.

21. The sustained release composition according to claim 1, wherein the saturated fatty acid of said fatty acid ester is stearic acid.

22. The sustained release composition according to claim 1, wherein said fatty acid ester of polyglycerol is selected from the group consisting of stearic acid penta(tetra)glyceryl ester, stearic acid mono(tetra)glyceryl ester, stearic acid penta(hexa)glyceryl ester, stearic acid sesqui(hexa)glyceryl ester, stearic acid mono-deca)-glyceryl ester and mixtures thereof.

23. The sustained release composition according to claim 1, wherein said fatty acid ester of polyglycerol is present in the coating agent at 20 to 100% by weight.

24. The sustained release composition according to claim 1, wherein said fatty acid ester of polyglycerol is present in the coating agent at 20 to 60% by weight.

25. The sustained release composition according to claim 1, wherein said coating agent further comprises water and a solid additive.

26. The sustained release composition according to claim 25 wherein the coating agent comprises 20 to 60 weight % of the fatty acid ester of polyglycerol, 40 to 90 weight % of water and 20 to 60 weight % of solid additive.

27. The sustained release composition according to claim 25, wherein said solid additive is selected from the group consisting of talc, corn starch, lactose, mannitol, sucrose and mixtures thereof.

28. The sustained release composition according to claim 11, comprising a pharmaceutical preparation coated with said coating agent.

29. A method of forming a solid sustained release composition comprising coating a solid preparation with a coating agent which comprises a fatty acid ester of polyglycerol.

30. A method for sustaining the release of a pharmaceutical ingredient comprising administering orally an effective amount of a pharmaceutical preparation which is coated with a coating agent comprising a fatty acid ester of polyglycerol.

31. A method for maintaining the release-sustaining ability of a sustained release pharmaceutical preparation over an extended period of time comprising coating a pharmaceutical ingredient with a coating agent which comprises a fatty acid ester of polyglycerol.

* * * * *